(12) United States Patent
Hesse

(10) Patent No.: US 11,583,666 B2
(45) Date of Patent: Feb. 21, 2023

(54) DEVICE AND METHODS FOR TREATING UROTHELIAL CONDITIONS

(71) Applicant: David Hesse, Branford, CT (US)

(72) Inventor: David Hesse, Branford, CT (US)

(*) Notice: Subject to any disclaimer, the term of this patent is extended or adjusted under 35 U.S.C. 154(b) by 0 days.

(21) Appl. No.: 17/492,100

(22) Filed: Oct. 1, 2021

(65) Prior Publication Data

US 2022/0023603 A1     Jan. 27, 2022

Related U.S. Application Data

(63) Continuation-in-part of application No. 16/836,185, filed on Mar. 31, 2020, now Pat. No. 11,246,693.
(Continued)

(51) Int. Cl.
*A61M 31/00* (2006.01)
*A61F 13/20* (2006.01)
(Continued)

(52) U.S. Cl.
CPC ......... *A61M 31/002* (2013.01); *A61F 2/0009* (2013.01); *A61F 13/2071* (2013.01); *A61F 13/2074* (2013.01); *A61F 13/34* (2013.01); *A61F 2002/048* (2013.01); *A61F 2013/2014* (2013.01); *A61F 2210/0004* (2013.01); *A61F 2210/0076* (2013.01);
(Continued)

(58) Field of Classification Search
CPC ..................................... A61F 5/44; A61F 5/48
See application file for complete search history.

(56) References Cited

U.S. PATENT DOCUMENTS

| 4,413,995 A | 11/1983 | Korpman |
| 5,090,424 A | 2/1992 | Simon et al. |
| (Continued) | | |

FOREIGN PATENT DOCUMENTS

| EP | 0193406 B1 | 2/1991 |
| WO | 9426215 A1 | 11/1994 |
| (Continued) | | |

OTHER PUBLICATIONS

Onofrei, M., and A. Filimon. "Cellulose-based hydrogels: designing concepts, properties, and perspectives for biomedical and environmental applications." Polymer science: research advances, practical applications and educational aspects (2016): pp. 108-120.
(Continued)

*Primary Examiner* — Yashita Sharma
(74) *Attorney, Agent, or Firm* — St. Onge Steward Johnston & Reens LLC

(57) ABSTRACT

A disposable device for treating a condition of a ureter or kidney having a cylindrical body about 1-2 mm in diameter by about 5 to 10 mm in length and having a top and bottom end. The body is made of absorbent material that expands upon contact with pharmaceutical agent and bodily fluids and includes a string connected to the bottom end of the body for removing the device. The device can be used to treat a condition of the ureter or kidney by inserting into the ureter or kidney, delivering a pharmaceutical agent, and removing the device after it has been impregnated with fluid. The device can be included in a kit with an insertion device and/or appropriate pharmaceutical agents.

18 Claims, 14 Drawing Sheets

Related U.S. Application Data

(60) Provisional application No. 62/902,165, filed on Sep. 18, 2019.

(51) Int. Cl.

| | | |
|---|---|---|
| *A61F 13/34* | (2006.01) | |
| *A61F 2/00* | (2006.01) | |
| *A61M 25/00* | (2006.01) | |
| *A61F 2/04* | (2013.01) | |

(52) U.S. Cl.
CPC .............. *A61F 2230/0069* (2013.01); *A61F 2310/0097* (2013.01); *A61M 25/0017* (2013.01); *A61M 2210/1082* (2013.01)

(56) References Cited

U.S. PATENT DOCUMENTS

| | | | |
|---|---|---|---|
| 5,887,593 A | | 3/1999 | Levius |
| 6,656,146 B1* | | 12/2003 | Clayman ............. A61M 27/008 604/8 |
| 6,676,593 B2 | | 1/2004 | Migachyov et al. |
| 6,679,831 B1 | | 1/2004 | Zunker et al. |
| 8,247,638 B2 | | 8/2012 | Kim et al. |
| 9,610,201 B2 | | 4/2017 | Schmidt-Foerst et al. |
| 9,707,065 B2 | | 7/2017 | Kunz |
| 10,195,091 B2 | | 2/2019 | Rosati et al. |
| 2002/0156343 A1* | | 10/2002 | Zunker ................. A61F 13/206 600/30 |
| 2002/0156442 A1* | | 10/2002 | Jackson ............. A61F 13/2068 604/385.18 |
| 2003/0191442 A1 | | 10/2003 | Bewick-Sonntag et al. |
| 2004/0078013 A1* | | 4/2004 | Zunker .................. A61F 2/005 604/355 |
| 2005/0113781 A1 | | 5/2005 | Forgeot et al. |
| 2006/0216334 A1 | | 9/2006 | Gehling et al. |
| 2007/0016163 A1* | | 1/2007 | Santini .................... A61F 2/446 604/500 |
| 2008/0077174 A1* | | 3/2008 | Mische .............. A61N 1/36082 606/198 |
| 2009/0318750 A1 | | 12/2009 | Ziv et al. |
| 2010/0100170 A1* | | 4/2010 | Tan .......................... A61F 2/07 623/1.18 |
| 2010/0185154 A1 | | 7/2010 | Tewari |
| 2011/0028778 A1 | | 2/2011 | Kunz |
| 2012/0259160 A1 | | 10/2012 | Karapasha |
| 2012/0290100 A1* | | 11/2012 | Li .......................... A61M 31/00 604/257 |
| 2013/0211185 A1 | | 8/2013 | Hull, Jr. et al. |
| 2016/0361191 A1 | | 12/2016 | Moon |
| 2018/0042742 A1* | | 2/2018 | Venkatraman ....... A61K 31/505 |
| 2019/0240063 A1 | | 8/2019 | Doreswamy et al. |

FOREIGN PATENT DOCUMENTS

| | | |
|---|---|---|
| WO | 2016005824 A1 | 1/2016 |
| WO | 2017134094 A1 | 8/2017 |

OTHER PUBLICATIONS

International Search Report and Written Opinion for PCT Application No. PCT/US2020/051545 dated Dec. 3, 2020.

ArmMed Media, Urinary Incontinence, "Managing Urinary Incontinence", Retrieved on Oct. 29, 2019: http://www.health.am/gyneco/more/managing-urinary-incontinence/ (6 pages total).

Nancy M. Shinopulos et al., "Patient Selection and Education for Use of the CapSure (Re/Stor) Continence Shield", Urologic Nursing, vol. 19, No. 2, pp. 135-140, Jun. 1999.

\* cited by examiner

DEVICE AND METHODS FOR TREATING UROTHELIAL CONDITIONS

FIELD OF THE INVENTION

The invention relates to a device that can be implanted in urothelial cavities, and methods of addressing urinary incontinence, erectile dysfunction, stones, and tumors in the urinary organs, by inserting the inventive devices into the urethra or ureters. The device is easy to insert and remove, does not require a prescription.

BACKGROUND OF THE INVENTION

Urothelial cancer is one of the most common cancers, affecting approximately 81,000 adults in the United States each year. Bladder cancer occurs in men more frequently than it does in women and usually affects older adults, though it can happen at any age. Urothelial cancer accounts for 90% of all bladder cancer and 10 to 15% kidney cancers.

In contrast, urothelial cancers of the upper urinary tract are relatively rare but are difficult to treat.

Current treatments for upper tract urothelial carcinomas include Nephron sparing or conservative management, especially if the cancer is low grade. These treatments aim to ablate and destroy the tumor deploying a small scope attached to a camera up into the ureter and kidney. This can be combined with chemotherapy or immunotherapy in the pelvis or the ureter. Chemotherapy can include delivering mitomycin-c in gel form, or alternatively, immunotherapy agents such as BCG, or chemotherapy such as mitomycin-c, gemcitabine, and docetaxel can be continuously dripped into the upper urinary tract via a tiny hollow tube. Robotic or open surgical treatment to remove all or part of the ureter, kidney and bladder for cancer is utilized depending on the location, size, grade and stage of the cancer. Surgery is reserved for those patients in whom local therapy failed or who originally presented with advanced disease.

There is desire for devices and improved methods of treating upper urothelial conditions. There is a desire for a device that will allow for immunotherapy and chemotherapy to dwell in the ureter and kidney, without agents draining immediately from the upper urinary tract.

It is also desirable to have a removable device that can absorb and deliver therapeutic agents to a ureter or kidney.

International Patent Application Publication WO 1994026215 by Uromed Corp. is directed to balloons for blocking the urethra. It describes an expandable deformable member (sponge) made of hydrophilic material which expands when moisture contacts it. The device, as illustrated in embodiments 1 through 3, would be difficult to manufacture and they rely on a cumbersome string apparatus. Patients would be required to manipulate different strings to activate/deactivate device, much like a two-string system used to raise and lower Venetian blinds. Embodiments 4 and 5 rely on coupling of proximal thermo-sensitive plug or sponge to a solid polyurethane cylindrical shaft with a distal meatal plate. Advancing a solid shaft up urethra is potentially dangerous, as minimal torqueing of the solid shaft could injure the urethra. Moreover, a meatal plate at urethral meatus would be uncomfortable and risk abrading delicate meatal tissue. Also, because the device is intended to be reusable, issues of the ability to satisfactorily disinfect a re-usable plug are to be questioned, especially if a sponge is used as the plug. These devices are not meant for the upper urothelial cavities and only address incontinence.

EP 0193406 to Medtronic, Inc. is directed to a urethral plug that comprises a hydrophilic, body fluid swelling hydrogel. However, this is aimed at a plug rather than a disposable absorber. As noted with the previous device, radial flanges or flaps, intended to serve as an umbrella at meatus and prevent migration of a device into the bladder, would be uncomfortable and risk abrading delicate meatal tissue. Furthermore, all hydrophilic hydrogels proposed for this device are non-biodegradable and therefore not optimal for disposable product.

There are reports of vaginal tampons being accidentally inserted into the urethra. These tampons are much too large for the opening and cause pain. Moreover, vaginal tampons are not designed to absorb urine or the amount of liquid discharged by many with incontinence issues.

U.S. Pat. No. 5,800,338 generally discloses the concept of a tampon that could be inserted into the urethra. The body of the tampon is provided with a withdrawal handle means protruding from the body and connected with an anchor part encapsulated in the body and having a relatively large bearing face against the surrounding molded material of the body. The handle and anchor part are made from a material with a knitted structure, to provide a three-dimensional bond to the molded material of the body. The anchor part is designed as a soft flexible element oriented in said longitudinal direction. However, no details are provided of how a urothelial tampon would differ from one suited for vaginal or anal insertion and a physical embodiment of a urothelial tampon is heretofore unknown by the inventor.

There is a need for devices that can be inserted in the ureters and urothelial cavities and/or kidneys, rather than the vagina.

There is a need for devices that can comfortably be inserted into the ureters and kidney to facilitate delivery of pharmaceutical agents, which can hold in place agents that work best if they are allowed to dwell in the ureter and renal pelvic spaces, that can be easily removed, preferably on an outpatient basis, and that do not abrade delicate tissue.

SUMMARY OF THE INVENTION

The foregoing is achieved by a device for insertion into the ureter or kidney of a mammal comprising: a substantially cylindrical body about 1-2 mm or 5 or less French scale ("Fr") in diameter by about 5 to 10 mm in length and having a proximal insertion end and a distal withdrawal end, said body comprised of absorbent material that expands upon contact with an aqueous treatment agent or bodily fluid; and a string connected to the distal end of the body for removing the device from the ureter or kidney.

In certain preferred embodiments, the diameter of the device is about 1 mm. In some alternative embodiments, the diameter is 5 Fr.

In some embodiments, the length of the body is about 5 mm.

In preferred embodiments, the substantially cylindrical body is composed of outer layer of desiccated cotton, followed by an intermediate layer of desiccated chitosan or cellulose/bio-sponge material, followed by an innermost layer of absorbent material, preferably super absorbent polymer (SAP) or nanofiber materials, both with hydrogel physicochemical properties.

The device may be encased in a mesh covering with a cotton string attached to one end. The mesh can be comprised or contained of polyethylene or other suitable materials known in the art. Other suitable string materials are also envisioned besides cotton and as disclosed in the vaginal and anal tampon arts.

The device can be housed in a dual lumen ureteral catheter whose proximal insertion tip is preferably tapered. The dual lumen catheter can be placed into the ureter over, e.g., an 0.038-inch guide wire or another suitable type of a wire. The guide wire may be placed into the ureter via a cystoscope or another suitable imaging device, such as a ureteroscope. Once the guide wire is placed at a desired location in the ureter, the cystoscope is withdrawn and the ureteral catheter or a ureteral stent is inserted over the guide wire through one of the catheter/stent lumens. Once the guide wire is removed, appropriate chemotherapy or another solution can be injected through the lumen used to place the guide wire via, e.g., a distal luer lock tip. The guide wire can then be used as plunger to push ureteral plug, housed in a second lumen of the catheter or stent, out the side of the tapered proximal ureteral catheter tip. The dual lumen can have calibrated markings to allow an operator to determine how far proximally the ureteral catheter has been placed. The catheter is then removed allowing the string attached to the ureteral plug to exit urethral meatus.

Once placed in a urothelial cavity, the device is capable of expanding to 100× to 700× its initial size. Absorbent properties of hydrogel polymers within the device will allow it to expand to internal volume of the ureter or kidney. Further, the increased viscosity of hydrogel polymers within device can obstruct flow of urine from passing thru or around the insert. The device is removed by simply pulling a string extending from the distal end of the body. The device can be removed easily by the patient at a later, predetermined time, which allows a patient to be discharged from an outpatient setting more quickly.

A kit for treating a condition of a ureter or a kidney comprises the herein disclosed device and a ureteral insertion device adapted for inserting the device into the ureter or kidney of a human. The ureteral insertion device may have two or more internal lumens. The kit may further comprise a chemotherapeutic, an immunotherapeutic agent, an alkalizing or acidifying agent, and/or an antibiotic delivered through a lumen of the ureteral insertion device.

A method for a condition of a ureter or a kidney in a patient in need thereof comprises inserting the device through a urethral opening into the ureter or the kidney of a patient having a stone or tumor, and removing the device after about 2 hours. The step of removing includes pulling the string that is attached to and exiting the withdrawal end of the device body and the urethral opening.

The method can further comprise the step of delivering one or more of a chemotherapeutic agent such as gemcitabine, docetaxel, mitomycin-c, or other agents, an immunotherapeutic agent such as BCG, or other agents, an alkalizing agent such as sodium bicarbonate, an acidifying agent such as Renacidin, or other agents, and/or an antibiotic to the kidney or ureter.

The device may be inserted into the ureter or kidney using a ureteral catheter or ureteral stent having at least two lumens. The method may further include inserting a scope into the patient to locate a target treatment site and inserting a wire through a scope lumen, wherein the ureteral catheter or the ureteral stent is inserted into the ureter or kidney over the wire. Additionally, the device may be contained in one of the at least two lumens of the ureteral catheter or the ureteral stent and the step of inserting the device may further include pushing a wire against the withdrawal end of the device body to advance the device into the ureter or kidney A method for treating a urothelial carcinoma in a patient in need thereof comprises inserting the device into a ureter or kidney using a wire to push the device out of a first lumen of an insertion device, delivering a chemotherapeutic agent is selected from mitomycin, gemcitabine, doxorubicin, docetaxel, or delivering an immunotherapeutic agent selected from BCG to a ureter or kidney, removing the insertion device from the ureter or kidney, leaving the device in the ureter or kidney for about 2 hours, and removing the device using the string.

A method for treating a kidney stone in a patient in need thereof comprises inserting the device of claim 1 into the kidney using a guide wire to push the device out of a first lumen of an insertion device, delivering sodium bicarbonate or Renacidin to a kidney having a kidney stone, removing the insertion device from the kidney, leaving the device in the kidney for about 2 hours, and removing the device using the string.

The inventive devices are easy to insert and remove, are cheap to manufacture, not bulky, provide comfort and psychological wellbeing, and are biodegradable/recyclable.

DETAILED DESCRIPTION OF THE INVENTION

The embodiments of the present invention will be described with reference to the accompanying drawings and below description.

Figure 1:
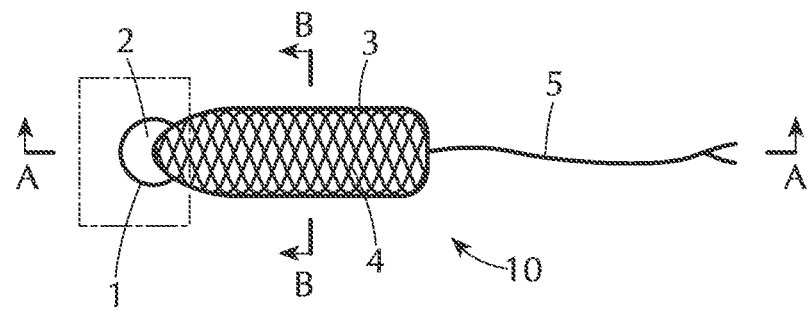
FIG. 1 is a side view of an absorbent device of the present invention.
Figure 5:
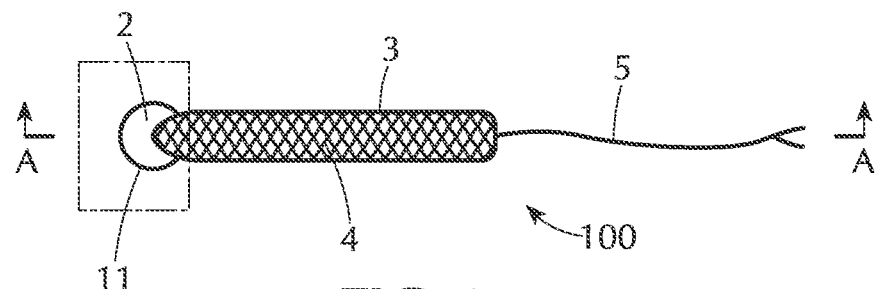
FIG. 5 is a side view of an absorbent device of the present invention.

Referring to FIGS. 1 and 5, a urine absorbing device 10 is depicted. The device 10 contains mesh covering 3, cylindrical body 4 and a withdrawal cord 5. The body 4 has an insertion end, a withdrawal end, a longitudinal axis, and an outer surface. As depicted in FIG. 1, the body 4 may contain a mesh covering 3 on or around the outer surface. Although shown as generally straight and cylindrical, the shape of the body may be straight or non-linear that curves along the longitudinal axis. A spiraled indentation into cylinder, e.g., may increase intra-urothelial wall surface tension by increasing device surface area.

Figure 7A:
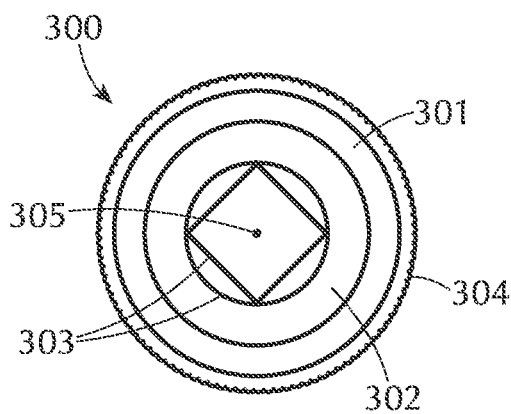
FIGS. 7A-7D are a cross sectional views of various embodiments of an absorbent device for insertion into the ureter along the radial axis.
Figure 7B:
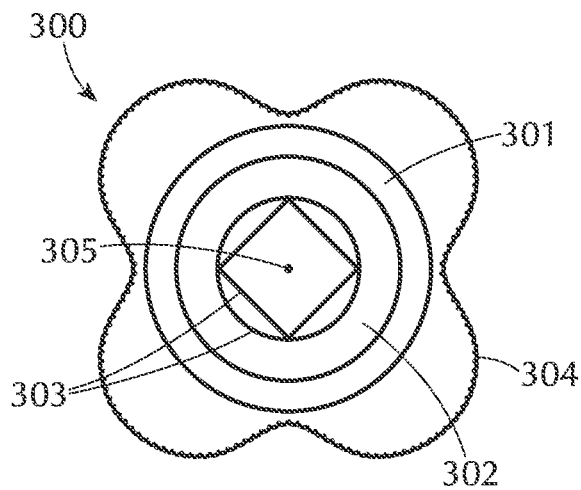
Figure 7C:
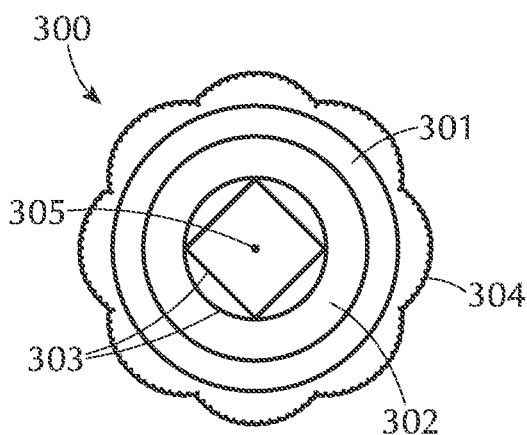
Figure 7D:
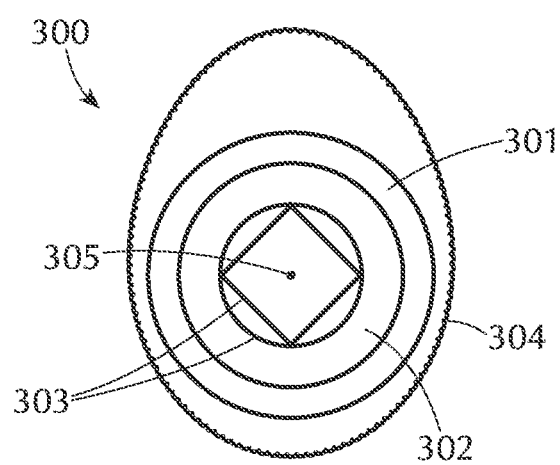

Other shapes are possible, such as those depicted in FIGS. 7B-7C. The bodies 304 may include shapes having a cross-section that can be described as rectangular, triangular, trapezoidal, semi-circular, hourglass-shaped, S-shaped, or other suitable shapes. The outer surface of the can be altered to have a non-uniform surface topography.

The "outer surface" refers to the visible surface of the body, which may be compressed and/or molded before use and/or expansion. At least a portion of the outer surface may be smooth, or alternatively may have ribs, spiral ribs, mesh patterns, etc., or other topographic features.

The body 4, 304 is comprised of absorbent material that expands upon contact with urine. A wide variety of liquid-absorbing materials used in absorbent articles are suitable, such as rayon, cotton, or comminuted wood pulp which is generally referred to as airfelt. Examples of other suitable absorbent materials include creeped cellulose wadding; meltblown polymers including conform; chemically stiffened, modified or cross-linked cellulosic fibers; synthetic fibers such as crimped polyester fibers; peat moss; tissue including tissue wraps and tissue laminates; or any equivalent material or combinations of materials, or mixtures of these. Preferred absorbent materials comprise cotton, rayon (including tri-global and conventional rayon fibers, and needle punched rayon), folded tissues, woven materials, nonwoven webs, synthetic and/or natural fibers.

The body 4, 304 may preferably be constructed of rayon or cotton or some combination of these. Suitable cotton material includes, long fiber cotton, short fiber cotton, cotton linters, T-fiber cotton, card strips, and comber cotton. Preferably, the cotton layers should be a scoured bleached cotton absorbent with a glycerin finish, a lemolin finish, or other suitable finish.

Figure 4:
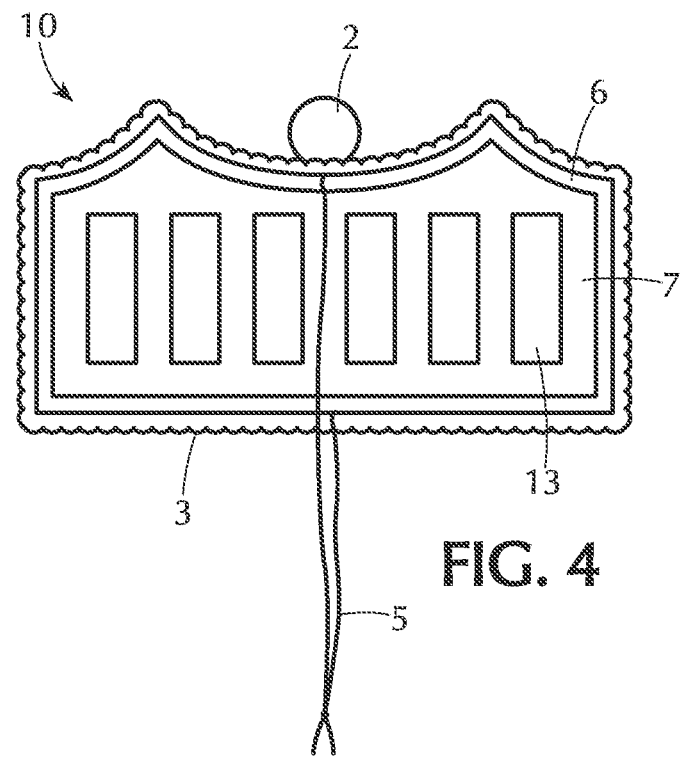
FIG. 4 is a cross-sectional view of the device of FIG. 1 along the axis A-A.

As shown in FIG. 4, the body preferably contains a central absorbent core having a first end, a second end disposed opposite said first end, and a side surface extending between said first end and said second end, wherein said first end corresponds to an insertion end of said tampon, said side surface being oriented in a direction generally parallel to a longitudinally-extending central axis, said central absorbent core being constructed from an absorbent material compressed to a self-sustaining form; and a withdrawal cord joined to said tampon and extending therefrom.

As used herein, the term "longitudinal axis" refers to an axis A-A that passes through the center of the device, as shown in FIG. 1. A portion of the device may be asymmetric about the longitudinal axis, such as when the withdrawal end region is twisted open from the initial shape of the rest of the tampon in a funnel shape (such as a "fin shape"). Further, the longitudinal axis may be linear or non-linear.

As used herein, the term "radial axis" of a tampon refers to an axis that runs perpendicular to the longitudinal axis of the tampon, shown as B-B in FIG. 1.

The length of the device can be measured along the longitudinal axis from the insertion end to the withdrawal end.

The withdrawal cord 5 may be attached to any suitable location on the device. The withdrawal cord, in one embodiment shown in FIG. 4, may be attached to the outer surface of the insertion end of the body. Alternatively, the attachment may be at the first end of the central absorbent core in one embodiment, or may be at the second end of the central absorbent core in other embodiments. In additional embodiments, multiple cords may be attached to the body and/or core allowing for both withdrawal and post-insertion manipulation of the absorbent device.

The withdrawal cord 5 may be made from any suitable material known in the prior art and may include cotton and rayon. In addition, the withdrawal cord 5 can take other forms such as ribbons, loops, tabs, and the like. The withdrawal cord may be integral with the body. The withdrawal cord 5 or a region of the withdrawal cord 5 may be treated to be non-absorbable, absorbent, or hydrophilic. The withdrawal cord 5 may be attached in any suitable manner known in the art, including suturing, adhesive attachment, bonding, thermal bonding, or combinations thereof.

The withdrawal cord 5 may be attached along the entire length and/or one major surface of the body and hang free from one end, such as the withdrawal end.

The term "attached", as used herein, encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element; one element is essentially part of the other element. The term "attached" may also include folding or wrapping the withdrawal cord around the device body.

In certain embodiments, the withdrawal cord 5 may be attached to the body using any suitable adhesive. Such adhesive may extend continuously along the length of attachment or it may be applied in a "dotted" fashion at discrete intervals. Alternatively, the cord 5 may be attached by stitching. Such stitching may use cotton or rayon thread. Other attachment mechanisms include thermally bonding, fusion bonding, or any other suitable means known in the art for joining such materials.

The mesh covering 3 may be hydrophilic coated biodegradable mesh covering measuring approximately 1 to 2 mm by 5 to 10 mm. In some embodiments, the mesh is comprised of polyethylene. Other materials, such as polyurethane, may be utilized for mesh 3.

Figure 2:
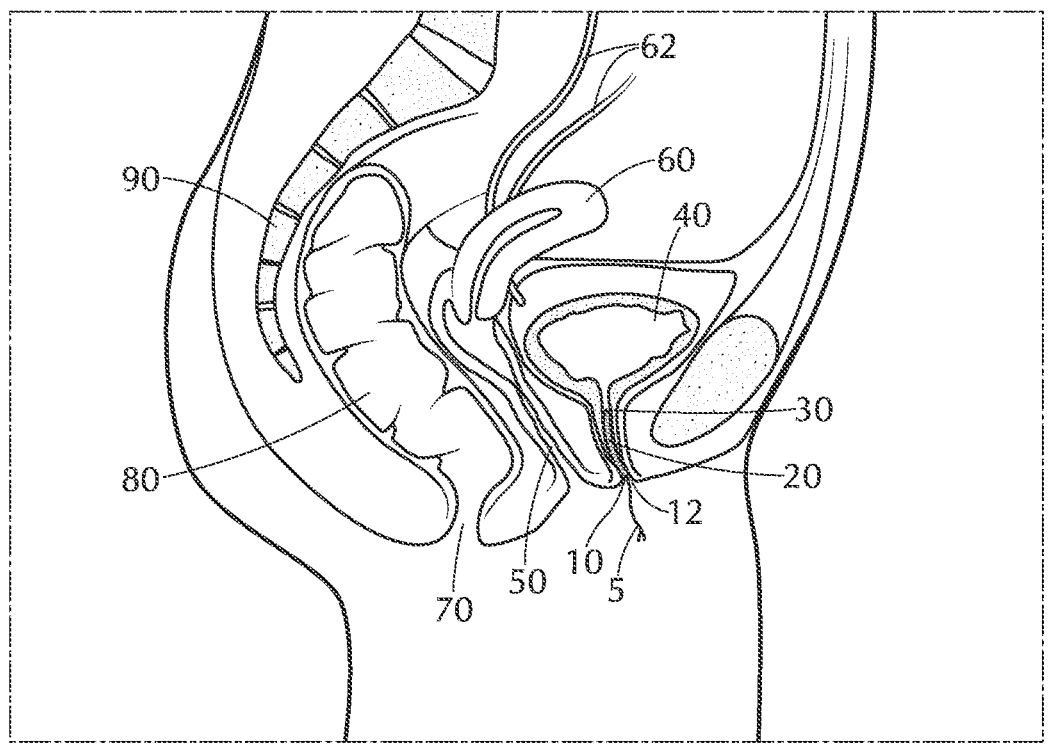
FIG. 2 is a cross section of a female pelvis, showing an absorbent device inserted into a urethra.

With reference to FIG. 2, the female anatomy contains a urethral meatus 12, an anterior urethra 20, and a proximal urethra 30. Above the proximal urethra 30 is the bladder 40 and ureters 62. The uterus 60 and vagina 50 lie behind the bladder and urethra, respectively. On the posterior side is the anus 70 and the rectum 80. The device 10 is optimally positioned in a ureter.

Figure 3:
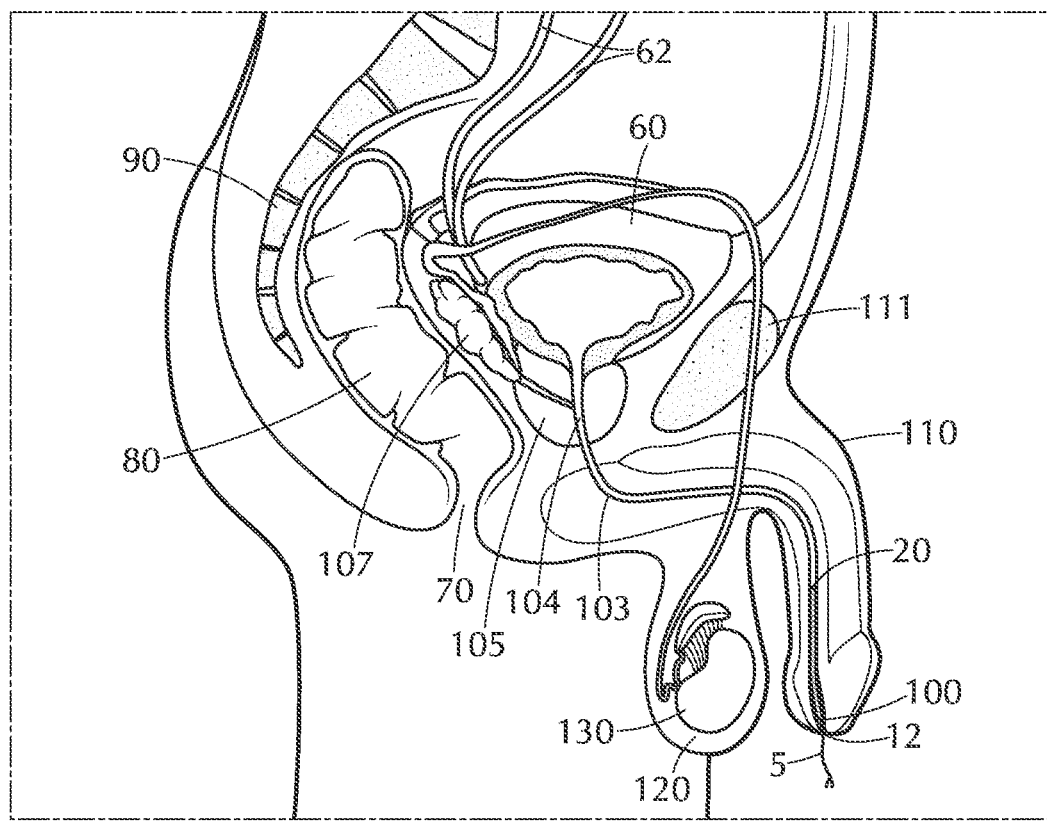
FIG. 3 is cross section of a male pelvis, showing an absorbent device inserted into a urethra.

FIG. 3 shows a cross-section of a male pelvis in which an inventive device 100 is inserted. The external male pelvic organs include the penis 110, scrotum 120 and testicle 130. The male urethra is a muscular tube that runs from the bladder 60, through the prostate 105 and penis 110. The pubic symphysis 111 is situated between the bladder 60 and abdominal wall. Like females, the males have ureters 62, a urethral meatus and anterior urethra 20. As the urethra conveys urine, as well as semen, out of the body, males additionally have a bulbar urethra 103 and bulbo-membraneous urethra 105 between the anterior urethra 20 and the prostate 105. Seminal vesicle 107 lies on the posterior surface of the urinary bladder 60. The anus 70, rectum 80 and coccyx 90 run along the posterior side.

Average diameter for male and female urethral openings is about 3 to 8 mm. The diameter of the absorbent device can be about 1-2 mm in diameter and about 5 to 10 mm in length, as the average ureter is about 1-3 mm in diameter and will typically be delivered with a 22 Fr cystoscope, or through a prepositioned 10 F ureteral double lumen catheter. The French (Fr) scale is used to measure the diameter of urological instruments. The diameter in mm (D) of a urinary tube is Fr/3 (D=Fr/3). The most common ureteral stents used are 4.8 and 6 Fr stents, although stents from 7 to 10 Fr are available. There are some uncommon conditions where urethral diameter may be less than 3 mm or more than 8 mm.

The cylindrical body 4 is preferably about 1-2 mm in diameter by about 5 to 10 mm in length. In alternative embodiments, there could be opportunity to scale device to the range of French stent sizes.

Other sizes and configurations are contemplated for other types of mammals, which will be dependent on the species. For instance, it is envisioned that the inventive devices could be adapted and useful for those with incontinent pet dogs and cats. Those skilled in the veterinary arts will have suitable knowledge to adapt the shape and size appropriately.

Because of the need for absorbent capacity, the body 4 of the absorbent devices may be formed from batts much larger in size than the ureteral orifice and compressed to the small size indicated above in order to facilitate insertion. The body containing absorbent material 13 may be compressed in the radial direction, the axial direction, or both, to provide a body 4 which is of a size and stability to allow insertion within a ureter. The body 4 may be compressed in both the radial and axial direction using any means known in the art. While a variety of techniques are known and acceptable for these purposes, a modified tampon compressor machine available from Hauni Machines, Richmond, Va., is suitable.

FIG. 4 shows a cross section of the device of FIG. 1. The body 4 contains an outer layer 6, a mesh 3 positioned round the outer layer 6, an intermediate layer 7 and absorbent core material 13 within the intermediate layer.

The outer layer 6 is exemplarily comprised of desiccated cotton. The intermediate layer 7 is comprised of desiccated chitosan or other cellulose bio sponge material.

The absorbent core material 13 may be comprised of superabsorbent polymer (SAP) or nanofiber. In preferred embodiments, the absorbent core material contains hydrogel properties. Although depicted as a plurality of rectangular discrete units, the absorbent core material 13 may take many forms. The absorbent core material may be contained in beads, capsules or sachets that are dispersed throughout the body 4 in a variety of configurations. The beads, capsules or sachets can take any shape. The absorbent core material may also be a SAP crystal, powder, fiber, or gel that is distributed in a homogenous or heterogenous manner.

Figure 6:
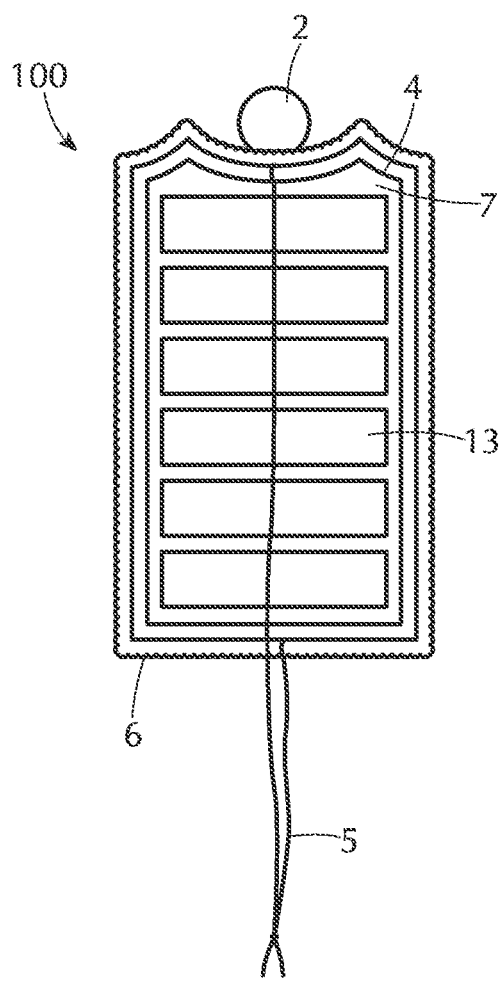
FIG. 6 is a cross-sectional view of a device of FIG. 5 along the axis A-A.

In FIG. 4, the absorbent core 13 is comprised of a single layer of absorbent material 13 spread consistently along the radial axis. In contrast, FIG. 6 shows an alternative configuration of absorbent the absorbent core.

FIGS. 7A-7D show the interior of an exemplary device 300 having outer layer 304 of the substantially cylindrical body that has depressions of various topography. The body also contains intermediate layers 301, 302; absorbent core 303; and string 305. The outermost surface of the outward layer 304 can contain a mesh as in the aforementioned embodiments. The absorbent core 303 is comprised of two different types of material with one encasing the other. The materials may be the same as those described for FIGS. 1 and 4.

Preferably, the outer layer 301 is comprised of desiccated cotton and the intermediate layer 302 is comprised of desiccated chitosan or other cellulose/bio-sponge material. The absorbent core 303 is super absorbent polymer (SAP). The string 305 is comprised of cotton. The encasing mesh 304 is a polyethylene mesh.

Other examples of suitable depressions can be seen in tampons having a non-uniform topography, such as in U.S. Pat. No. 3,695,270 (Dostal, issued Oct. 3, 1972), and U.S. Pat. No. 4,361,151 (Fitzgerald, issued Nov. 20, 1982) and U.S. Pat. No. 4,328,804 (Shimatani, issued May 11, 1982), U.S. Pat. No. 5,403,300 (Howarth, issued Apr. 4, 1995), U.S. Pat. No. 5,592,725 (Brinker, issued Jan. 14, 1997)), U.S. Pat. No. 5,718,675 (Leijd, issued Feb. 17, 1998). Other tampons include longitudinal ribs on the outer surface, and in U.S. Pat. No. 7,549,982, the tampon has a spiral groove on the outer surface. All such surface topography is contemplated for the urethral devices described herein.

Texturing can be provided through a variety of means, including a multiplicity of texturing elements. Such texturing may be provided by needle punching the surface of the surface to be textured.

Texturing elements may also be configured to transfer fluid from the urethral surfaces to the outer surface of the body and ultimately, to the absorbent core through the use of a density gradient, hydrophilicity gradients, an osmotic driving force, capilarity, or a similar mechanism. Suitable materials for use in such fluid acquisition/transfer mechanisms are rayon (including, e.g., WO 00/06070 conventional, tri-lobed or multi-lobed rayon fibers), polyethylene, polypropylene, polyester, synthetic bi-component fibers, absorbent foams and combinations thereof, all of which fibers may be used either singly or in combination with other fibers are known in the art. Capillary channel fibers are a highly preferred fiber for texturing elements.

Figure 8:
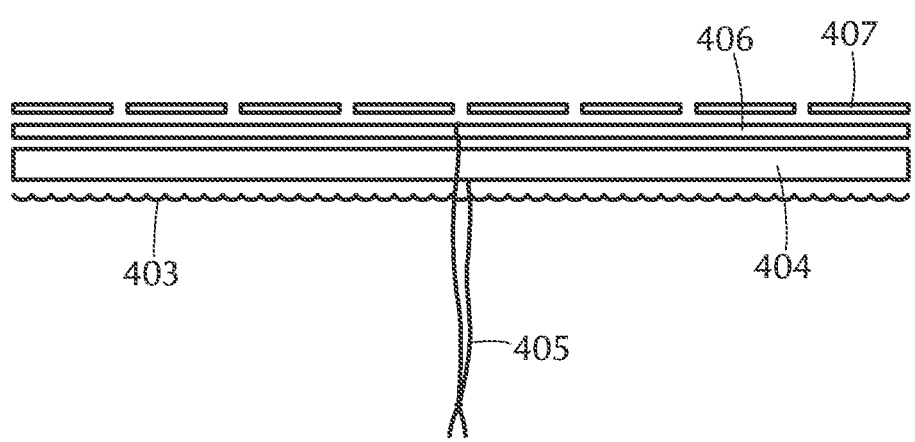
FIG. 8 is an unraveled distal end view of a device of the invention.

FIG. 8 shows an unraveled side view of another device wherein: 407 is super absorbent polymer (SAP) or nanofiber; 406 is desiccated chitosan or other cellulose/bio-sponge material; 404 is desiccated cotton; 405 is cotton string and 403 is polyethylene mesh covering.

Figure 10A:
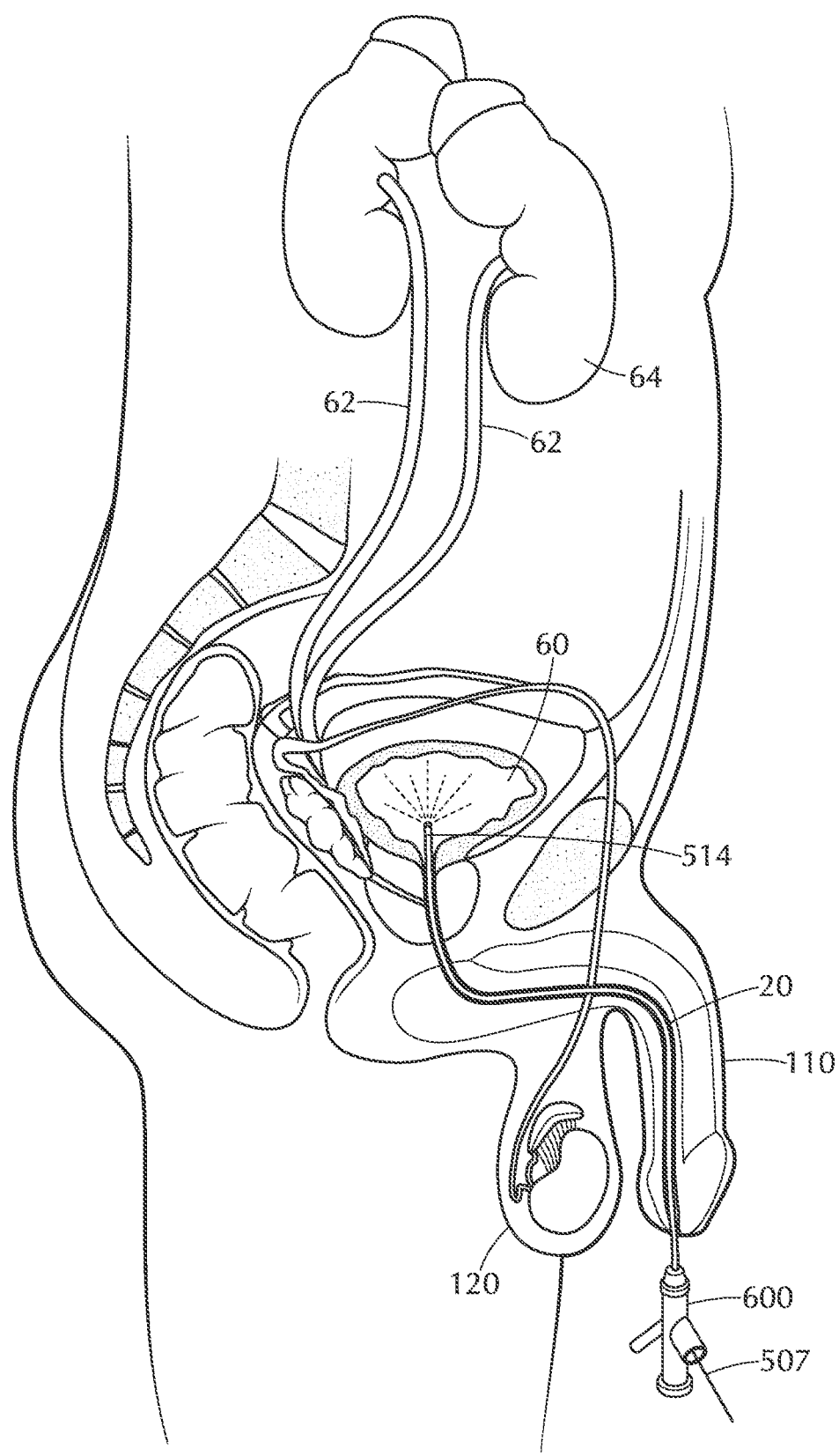
FIGS. 10A-10F show a method of delivering an inventive absorbent device to a male ureter.
Figure 10B:
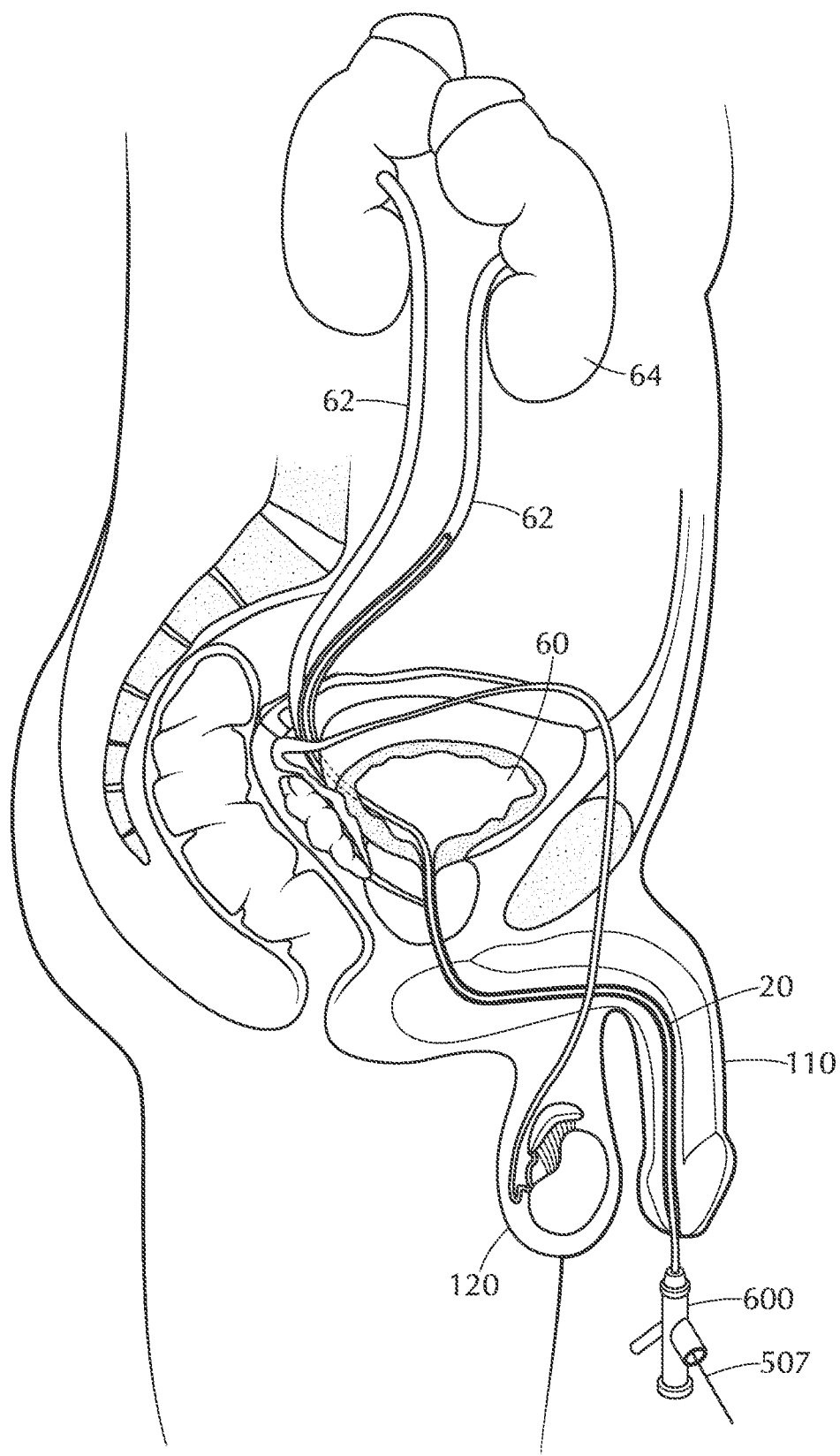
Figure 10C:
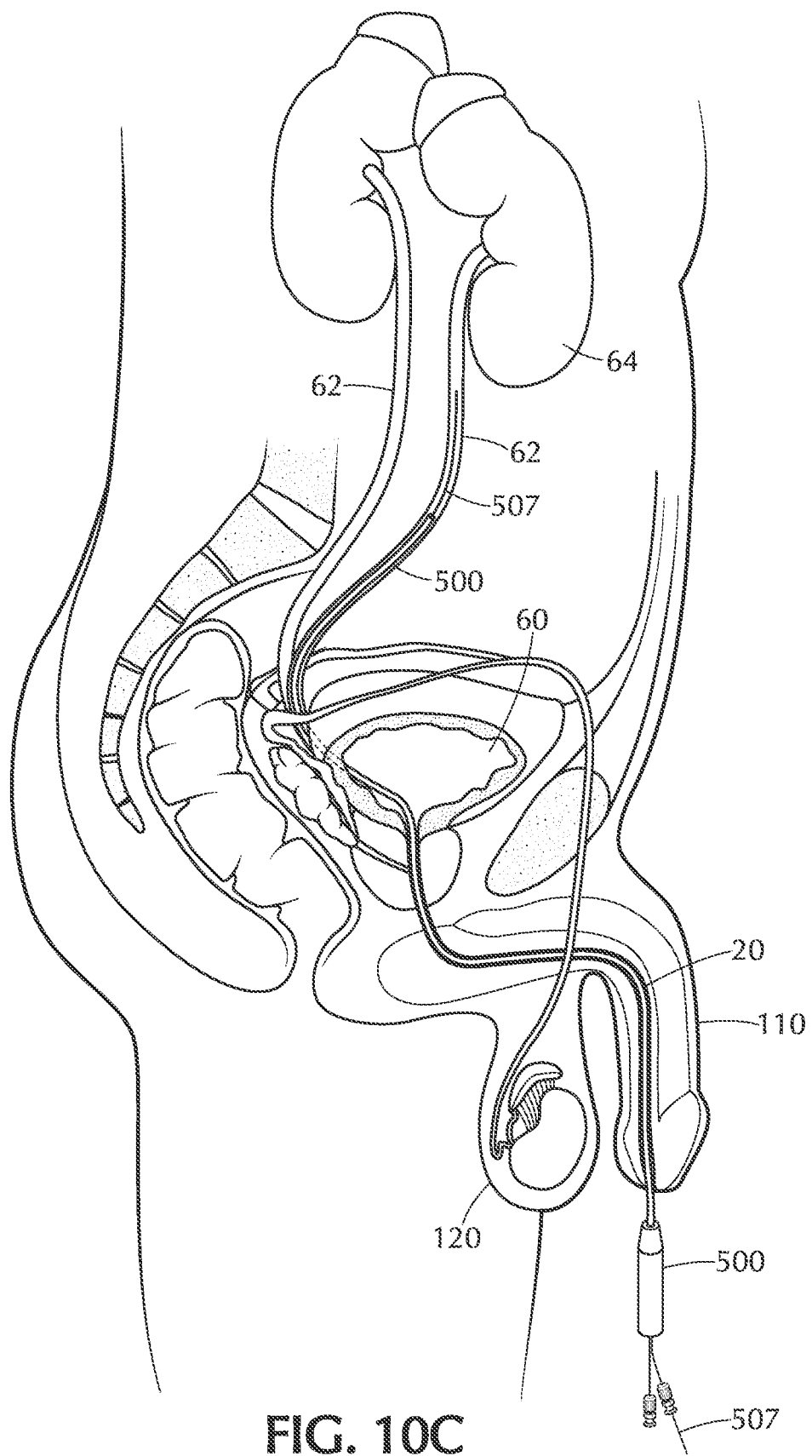

FIGS. 10A-10C show an exemplary method of treating a condition of the ureter with an inventive device. Patients who present with low grade and stages Ta, Tis, and T1 upper urinary tract urothelial cancer often progress to nephroureterectomy because, unlike in the bladder, there is no effective way control lower risk disease by allowing chemotherapeutic agents to dwell in the upper urinary tract.

As shown in FIG. 10A, after administration of local anesthesia and/or topical anesthetic, a suitable imaging device, such as a cystoscope or a ureteroscope 600, can be advanced through the urethra 20 and into the bladder 60 in order to locate an affected ureter 62 and/or kidney 64. The device 600 preferably includes a camera 514 and a light source for assisting in visualizing the internal anatomy during insertion. In some embodiments, a cystoscope with a size of 17 to 22 Fr according to the French scale is used. If a patient has a stone or tumor lodged higher in the urinary tract, a much finer caliber scope called a ureteroscope can be inserted through the bladder and up into the ureter to locate a target treatment site and/or to assets in locating or cannulating ureteral opening. The ureteroscope typically has a size of 5 to 9 Fr according to the French scale. It is understood that any other suitable imaging or insertion device may be used in accordance with the present invention.

Once the proximal tip of the ureteroscope 600 is placed adjacent the target treatment site, a guide wire 507 is advanced through a ureteroscope lumen and out from the proximal tip, as shown in FIG. 10B. Once the guide wire 507 is anchored at the desired treatment site, the ureteroscope 600 is withdrawn from the bladder and a ureteral catheter 500 or ureteral stent is inserted into the ureter or kidney over the guidewire, as shown in FIG. 100. It is understood that any suitable type of wire may be used to insert the ureteral catheter or stent into the ureter or kidney.

Figure 9A:
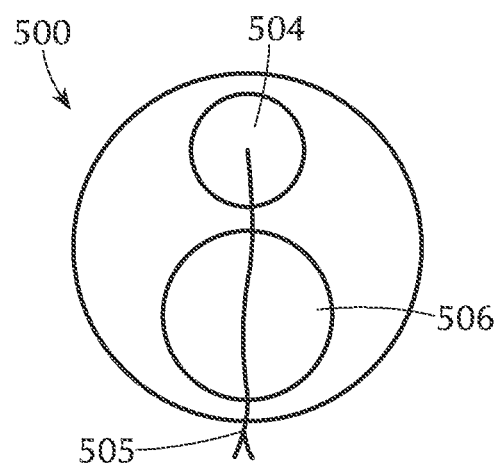
FIG. 9A is distal cross section of a ureteroscope body that can be used to deliver an inventive absorbent device to the urological anatomy.
Figure 9B:
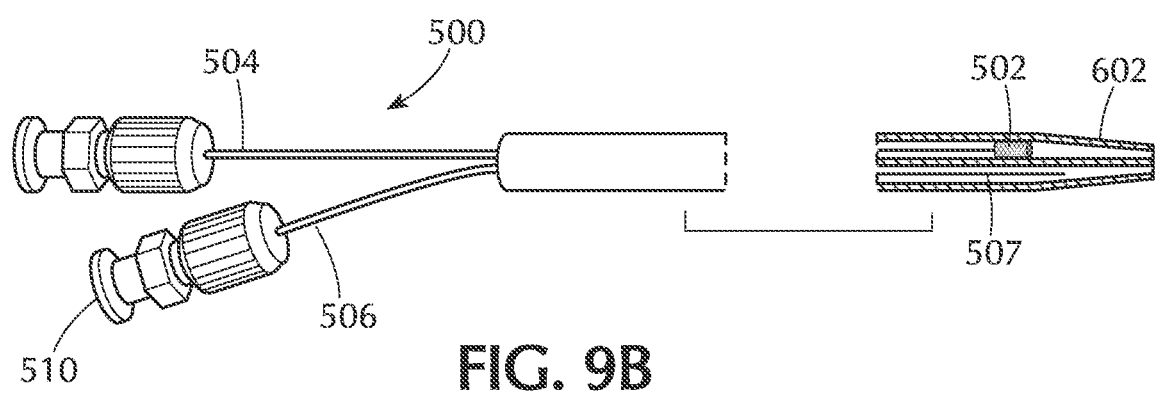
FIG. 9B is a partial view of the distal and proximal ends of a catheter that can be used to deliver an inventive absorbent device to the urological anatomy.

FIGS. 9A-9B show an exemplary double lumen ureteral catheter or stent 500 that could be used to advance a ureteral device 502 into the ureter. The catheter 500 contains a first lumen 504, which can be used for insertion of the ureteral device 502, and a drug delivery side port 510 that is connected to a second lumen 506 running through the catheter body. The catheter 500 has a tapered proximal tip 602 design which facilitates access to the urinary tract. The guide wire 507 may be passed through either of the first and second lumens 504, 506 of the catheter 500 during insertion of the catheter. In preferred embodiments, the ureteral device 502 is preplaced in one of the catheter lumens 504 or 506. In these embodiments, the guide wire 507 is passed through the other lumen not occupied by the ureteral device 502. FIG. 9A shows a cross-sectional view of the distal end of the catheter 500 showing the string 505 attached to the ureteral device 502 exiting out of the first catheter lumen 504.

In some preferred embodiments, a working length of the ureter catheter or stent is about 20-30 inches. In more preferred embodiments, a working length of the ureter catheter is about 21 inches. In some embodiments, a diameter of the first lumen 504 is about 0.06 to 0.08 inches (1.5 to 2 mm) and a diameter of the second lumen 506 is about 0.03 to 0.05 inches. In further embodiments, an outer diameter of the catheter 500 is about 0.1 to 0.2 inches. In additional embodiments, the catheter is a 10F diameter catheter according to the French scale.

Figure 10D:
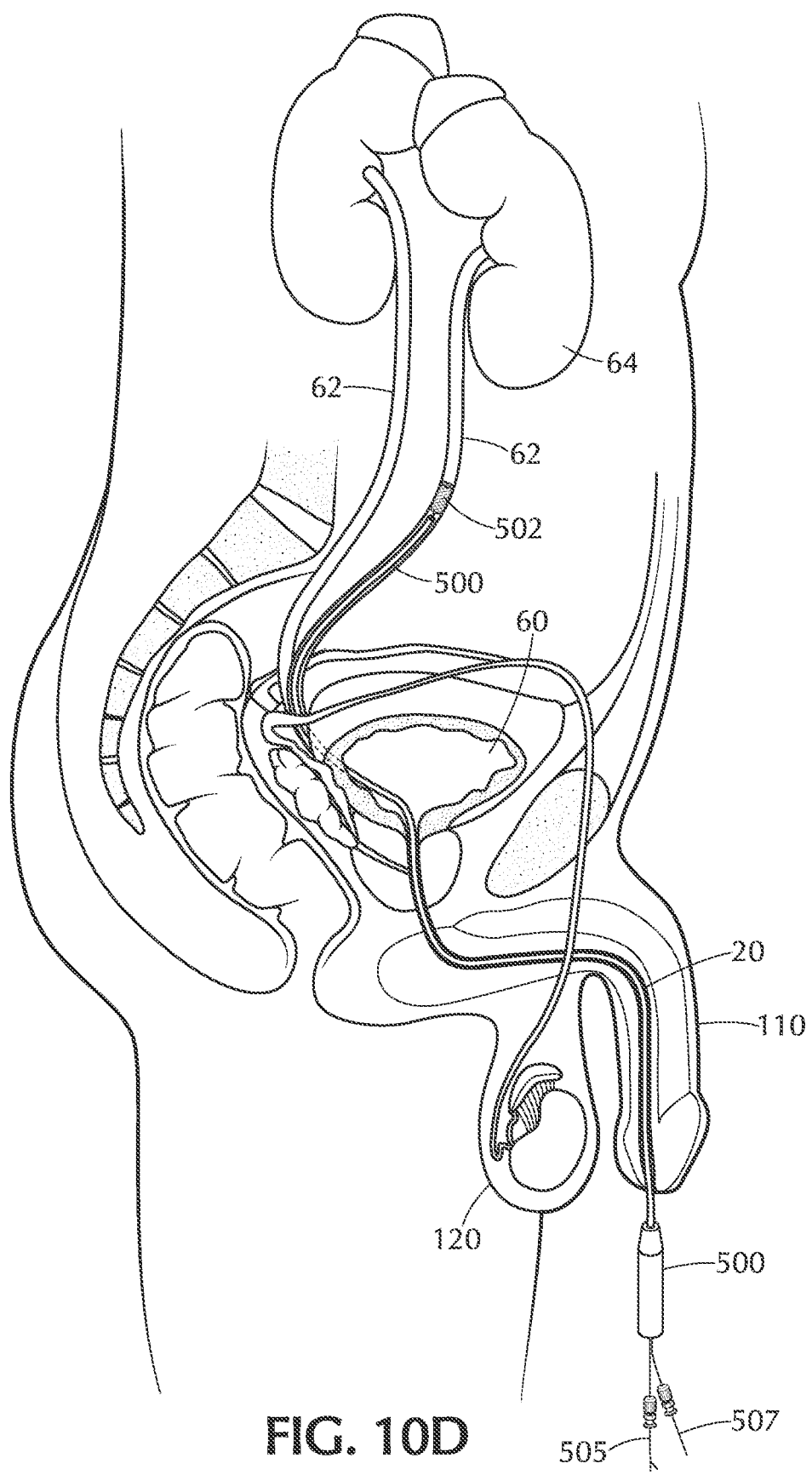
Figure 10E:
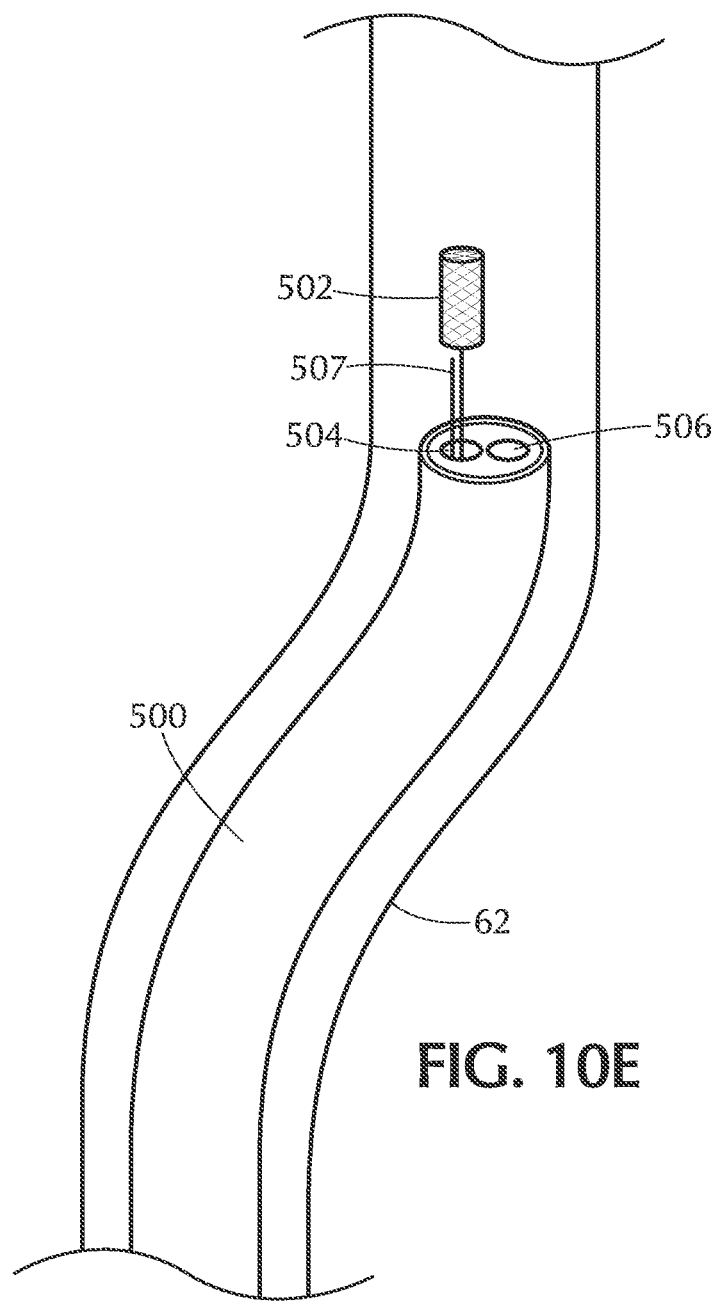

After the ureter catheter 500 is inserted over the guide wire 507 and is placed at a target site, the ureteral device 502 is inserted into one of the internal catheter lumens 504 or 506. Alternatively, as mentioned above, the ureteral device 502 may be pre-placed in one of the internal catheter lumens 504 or 506. A distal end of the string 505 attached to the ureteral device 502 extends out of the catheter insertion port at the distal end of the catheter. Next, the guidewire 507 is inserted into the lumen that houses the ureteral device 502 and is used to push the ureteral device 502 out of the catheter lumen and into the target site, as shown in FIGS. 10D and 10E. It is noted that a guide wire used to push out the ureteral device 502 may be the same or different from the guide wire 507 used to insert the catheter 500 to the target site. A medication may be instilled into the ureter 62 and/or kidney 64 via one of the catheter lumens prior to placing the ureteral device 502, as described in more detail below. The medication is instilled through one of the internal lumens 504, 506 of the catheter 500 that is not used to insert the device 502.

In one exemplary embodiment shown in FIGS. 9A-9B, the catheter 500 is inserted at the target site over the guidewire 507 that is passed through the second lumen 506. The first lumen 504 of the catheter 500 has a pre-placed ureteral device 502. Once the catheter 500 is placed at the target site, the guide wire 507 is withdrawn from the second lumen 506 and the second lumen 506 is used to deliver a medication to the target site via the drug delivery side port 510. The guidewire 507 or a different wire is then inserted into the first lumen 504 and is used to push the ureteral device 502 out of the catheter and into the target side.

Figure 10F:
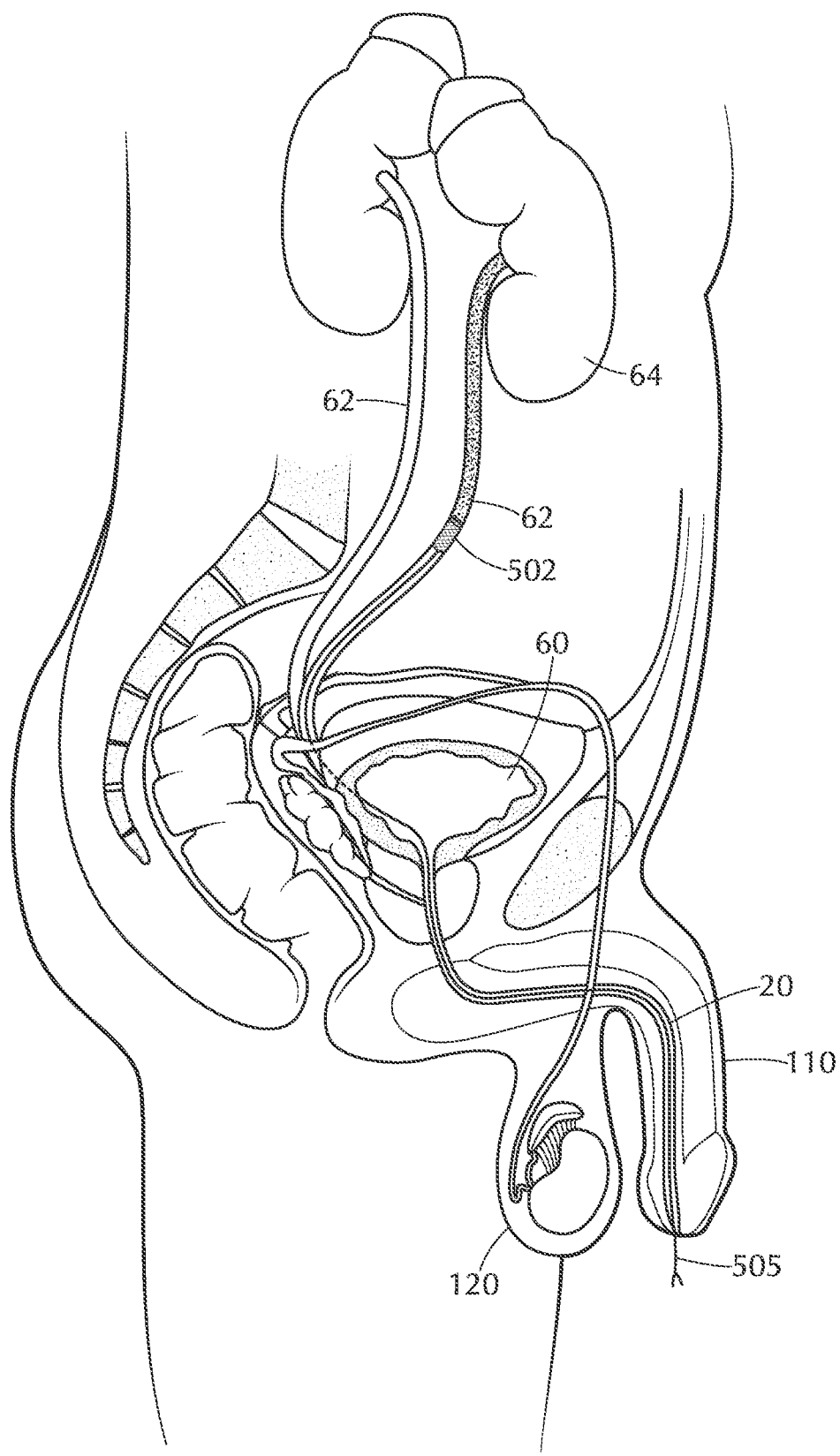

Once the ureteral device 502 is placed at the desired location 62, the catheter 500 is removed from the ureter and/or kidney and the device 502 is left to dwell in the ureter with the string 505 extending out of the urethral opening, as shown in FIG. 10F. String 505 is used to dislodge and remove device after the desired treatment time.

As mentioned, a device 502 suitable for placement in the ureter is about 1-2 mm in diameter and about 5 to 10 mm in length, as the average ureter is about 1-3 mm.

Figure 11A:
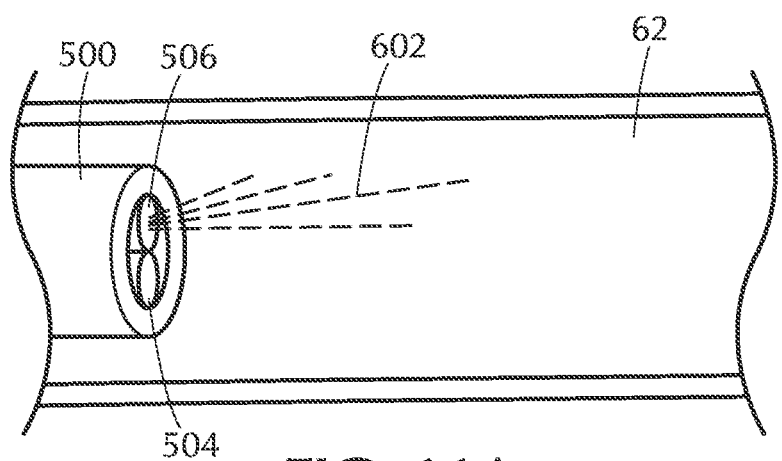
FIGS. 11A-11C show a method of treating a urothelial condition using an inventive absorbent device.
Figure 11B:
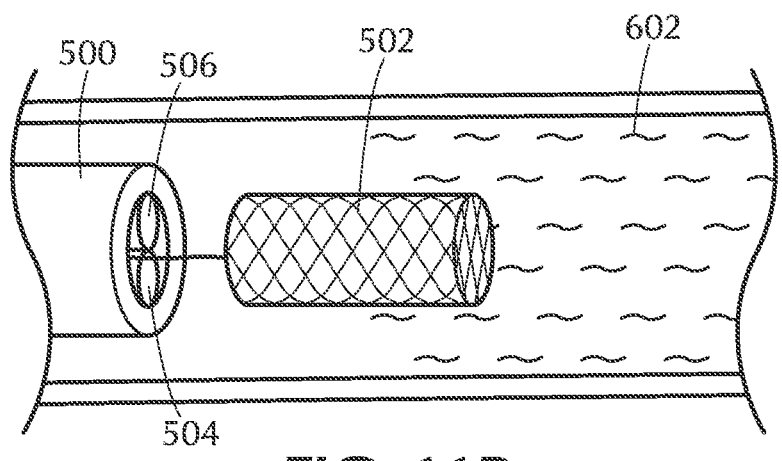
Figure 11C:
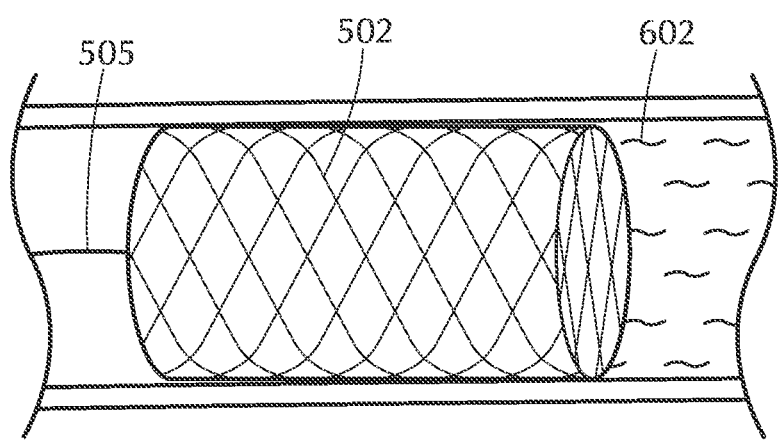

FIGS. 11A-11C show delivery of drug in ureteral lumen 62. As shown in FIG. 11A, once the proximal end of the catheter 500 with the ureteral device 502 is positioned at the target site 62, the lumen 506 is used to deliver an active agent 602 to the treatment site. Next, as shown in FIG. 11B, the ureteral device 502 is pushed out of the catheter lumen 504 and placed at the treatment site 62. The active agent 602, along with ureteral secretions will cause the device 502 to expand and fill the diameter of the lumen, helping to push and sustain the drug in the desired location until the device is dislodged with string 505, as shown in FIG. 11C.

Figure 12A:
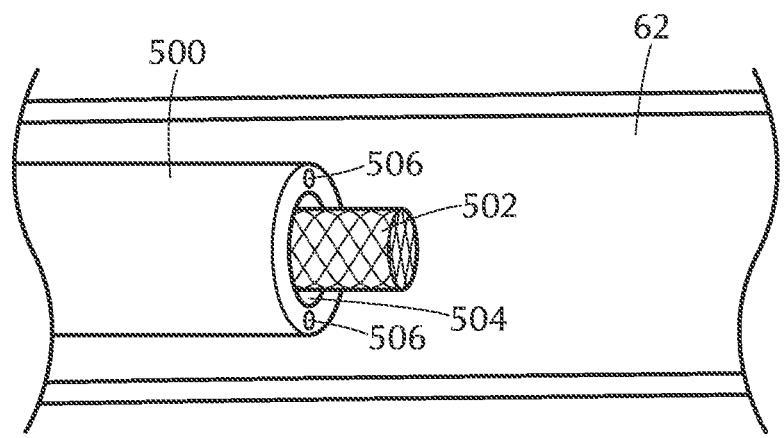
FIGS. 12A-12C show another embodiment of a method of treating a urothelial condition using an inventive absorbent device.
Figure 12B:
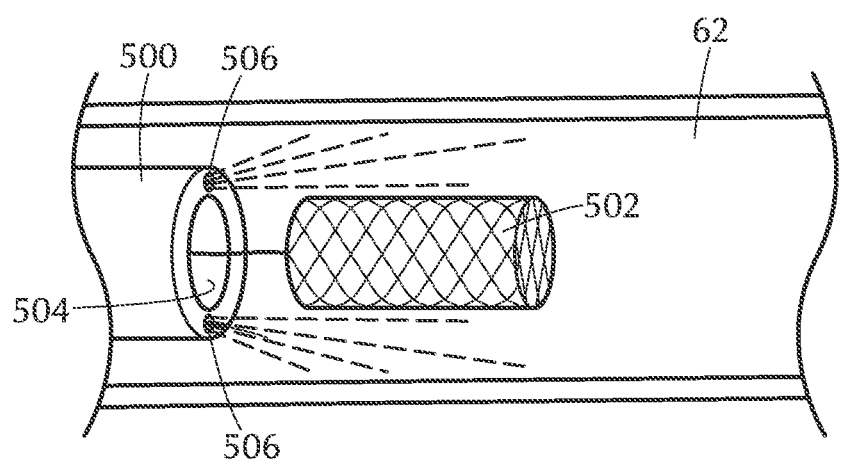
Figure 12C:
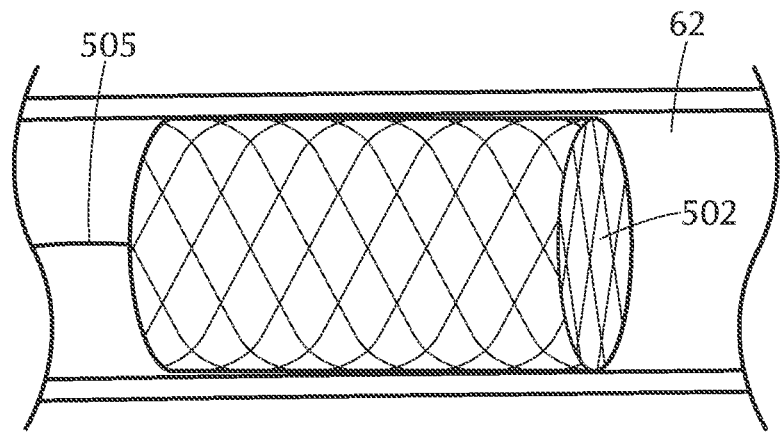

In additional embodiments shown in FIGS. 12A-C, the ureteral device 502 may be pushed out the catheter lumen 504 prior to delivery of the active agent, as shown in FIG. 12A. Once the device 502 is placed at the treatment site, the active agent is delivered to the site via the lumen(s) 506. In additional embodiments, the active agent may also be delivered through the lumen 504 once the device 502 is pushed out of that lumen. The active agent 602, along with ureteral secretions, causes the device 502 to expand and fill the diameter of the lumen, which causes the active agent to be pushed into the lumen wall and/or any tumor tissue or another structure located at the treatment site. Further, the expanded device 502 blocks the passage of the active agent downstream of the device and thus, assists in localized delivery of the active agent. It is noted that the ureteral device 502 may also be pre-coated with one or more active agents such that the agents are delivered to the target site once the device 502 is placed there.

The drug may be selected from one or more of mitomycin-c, gemcitabine, doxorubicin, docetaxel, and BCG, or other agents to be developed to treat upper urinary tract cancers.

It is also envisioned, for e.g. large stones, the drug and device 502 can be used to decrease stone burden and the physician may also use an extra tube in the ureteroscope to extend a flexible fiber that carries a laser beam to break a stone or tumor into smaller pieces that can then pass out of the body in the urine. An alkalizing agent such as sodium bicarbonate, or alternatively, and acidifying agent may be delivered to break up kidney stones along with an antibiotic to treat or prevent further conditions, depending on stone composition.

Examples

Example 1: A 64 year old male presented with painless gross hematuria. He was found to have multiple low grade urothelial tumors involving his right upper urinary tract. Patient underwent right nephroureterectomy. He then developed multifocal superficial urothelial tumors in his bladder treated with cystoscopic resection followed by an outpatient course of intravesical BCG, given weekly for six weeks. Follow-up cystoscopic examinations show no recurrent urothelial carcinoma in his bladder. He again presents with gross hematuria. He has developed multiple low grade superficial tumors in his solitary left ureter and kidney. Multiple lesions were ablated using laser technology. He is at high risk for cancer recurrence and/or progression of disease in his solitary kidney.

The methods and device disclosed herein would markedly lower the risk of patient requiring left nephroureterectomy, and subsequent kidney dialysis. Intravesical chemo or immunotherapy treatments lower the risk of urothelial recurrence or progression by 25 to 75% in the bladder. Using described device and methods we can use same technology used for lower urinary tract and apply it to upper urinary tract.

Example 2: A 75 year old female presented with staghorn calculus of her left kidney. She undergoes percutaneous nephrostolithotomy and subsequent left ureteroscopy to remove stone, however, she is left with residual stone burden. Her stone composition returns as magnesium ammonium sulfate. Renacidin irrigation of her collecting system, if it can dwell in her collecting system, will dissolve residual stone burden. Detailed embodiments of the present invention are disclosed herein; however, it is to be understood that the disclosed embodiments are merely exemplary of the invention that may be embodied in various forms. It will be appreciated that many modifications and other variations that will be appreciated by those skilled in the art are within the intended scope of this invention as claimed below without departing from the teachings, spirit and intended scope of the invention.

What is claimed is:

1. A device for delivering and enabling therapeutic agents to dwell in a ureter or a kidney comprising:
    a substantially cylindrical body about 1-2 mm in diameter by about 5 to 10 mm in length and having an insertion end and a withdrawal end, said body comprised of absorbent material that expands upon contact with fluid; and
    a string attached to and exiting the withdrawal end of the body for removing the device from the cavity.

2. The device of claim 1, wherein the body comprises an outer layer, an intermediate layer and an inner layer, said intermediate and inner layers comprising hydrogel properties.

3. The device of claim 1, further comprising a mesh encasing the body.

4. The device of claim 3, wherein the mesh is comprised of polyethylene and/or polyurethane.

5. The device of claim 1, wherein the insertion end of the body is tapered.

6. The device of claim 1, wherein the absorbent material comprises super absorbent polymer (SAP).

7. A kit for treating a condition of a ureter or a kidney comprising the device of claim 1, and a ureteral insertion device for inserting the device into the ureter or kidney of a human.

8. The kit of claim 7, wherein the ureteral insertion device has two or more internal lumens.

9. The kit of claim 7, wherein the kit further comprises a chemotherapeutic agent, an immunotherapeutic agent, an alkalizing agent, an acidifying agent, and/or an antibiotic delivered through a lumen of the ureteral insertion device.

10. A method for treating a condition of a ureter or a kidney in a patient in need thereof comprising:
    inserting the device of claim 1 through a urethral opening into the ureter or the kidney of a patient having a stone or tumor; and
    removing the device after about 2 hours.

11. The method of claim 10, wherein the step of removing includes pulling the string that is attached to and exiting the withdrawal end of the device body and the urethral opening.

12. The method of claim 10, further comprising the step of delivering one or more of a chemotherapeutic agent, an immunotherapeutic agent, an alkalizing agent, an acidifying agent, and/or an antibiotic to the kidney or ureter prior to the step of removing the device.

13. The method of claim 12, wherein the chemotherapeutic agent is selected from gemcitabine, docetaxel, and mitomycin-c.

14. The method of claim 10, wherein the device is inserted into the ureter or kidney using a ureteral catheter or ureteral stent having at least two lumens.

15. The method of claim 14, further comprising inserting a scope into the patient to locate a target treatment site and inserting a wire through a scope lumen, wherein the ureteral catheter or the ureteral stent is inserted into the ureter or kidney over the wire.

16. The method of claim 10, wherein the device is contained in one of the at least two lumens of the ureteral catheter or the ureteral stent and the step of inserting the device further comprises pushing a wire against the withdrawal end of the device body to advance the device into the ureter or kidney.

17. A method for treating a urothelial carcinoma in a patient in need thereof, comprising the steps of:
    inserting the device of claim 1 into a ureter or kidney using a wire to push the device out of a first lumen of an insertion device;
    delivering a pharmaceutical agent selected from the group consisting of mitomycin, gemcitabine, doxorubicin, docetaxel, and BCG to the ureter or kidney via a second lumen of the insertion device;
    removing the insertion device from the ureter or kidney;
    leaving the device in the ureter or kidney for about 2 hours; and removing the device using the string.

18. A method for treating a kidney stone in a patient in need thereof, comprising the steps of:
    inserting the device of claim 1 into the kidney using a guide wire to push the device out of a first lumen of an insertion device;
    delivering sodium bicarbonate or Renacidin to a kidney having a kidney stone via a second lumen of the insertion device;
    removing the insertion device from the kidney;
    leaving the device in the kidney for about 2 hours; and removing the device using the string.

* * * * *